United States Patent
Jiang

(10) Patent No.: US 12,313,533 B2
(45) Date of Patent: May 27, 2025

(54) GAS SENSING

(71) Applicant: KONINKLIJKE PHILIPS N.V., Eindhoven (NL)

(72) Inventor: Zhi-Xing Jiang, Wallingford, CT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 309 days.

(21) Appl. No.: 17/947,281

(22) Filed: Sep. 19, 2022

(65) Prior Publication Data

US 2023/0096813 A1    Mar. 30, 2023

Related U.S. Application Data

(60) Provisional application No. 63/247,820, filed on Sep. 24, 2021.

(51) Int. Cl.
| | |
|---|---|
| G01N 21/3504 | (2014.01) |
| G01J 3/10 | (2006.01) |
| G01N 21/03 | (2006.01) |

(52) U.S. Cl.
CPC .......... *G01N 21/3504* (2013.01); *G01J 3/108* (2013.01); *G01N 21/0303* (2013.01); *G01N 2201/066* (2013.01)

(58) Field of Classification Search
None
See application file for complete search history.

(56) References Cited

U.S. PATENT DOCUMENTS

| | | | |
|---|---|---|---|
| 4,899,053 A | 2/1990 | Lai | |
| 5,942,755 A * | 8/1999 | Dreyer | G01N 21/3151 |
| | | | 250/343 |
| 2002/0113213 A1* | 8/2002 | Amirkhanian | G01N 27/44782 |
| | | | 250/458.1 |
| 2003/0139682 A1 | 7/2003 | Kanstad | |
| 2010/0078563 A1 | 4/2010 | Haveri | |
| 2017/0146450 A1* | 5/2017 | Coates | F01N 11/007 |

FOREIGN PATENT DOCUMENTS

| | | |
|---|---|---|
| CN | 108931477 A | 12/2018 |
| CN | 109507140 A | 3/2019 |

* cited by examiner

*Primary Examiner* — Edwin C Gunberg

(57) ABSTRACT

In an embodiment, an apparatus (100) is described. The apparatus comprises an infrared, IR, generating system (102). The IR generating system comprises a first IR source (104) configured to produce IR radiation for forming a first IR beam (106) in a first spectral band. The IR generating system further comprises a second IR source (108) configured to produce IR radiation for forming a second IR beam (110) in a second spectral band. The apparatus further comprises a beam manipulation system (112) configured to combine a beam path of the first and second IR beams and direct the first and second IR beams along the beam path through a gas sample region (114). The apparatus further comprises an IR detection system (116) configured to detect an intensity of the first and second IR beams after passage through the gas sample region. The IR detection system is configured to produce a signal (118) from which an indication of a concentration of a target gas in the gas sample region can be derived.

20 Claims, 6 Drawing Sheets

GAS SENSING

TECHNICAL FIELD OF THE INVENTION

The invention relates to an apparatus, method and respiratory monitoring system for gas sensing.

BACKGROUND OF THE INVENTION

Some infrared (IR) sensors used for detecting partial pressure (or concentration) of a target gas constituent (e.g., carbon dioxide) in a gas sample operate by measuring the proportion of IR radiation absorbed in the gas sample at certain wavelengths within the absorption spectrum for the target gas that are characteristic of the target gas rather than another gas constituent (e.g., water vapor). Some absorption bands of carbon dioxide have absorption peaks centered at around the following wavelengths: 2 µm (microns), 2.7 µm and 4.3 µm. By way of comparison, some absorption bands of water vapor have absorption peaks centered at the following wavelengths: 1.38 µm, 1.87 µm and 2.7 µm. Appropriate selection of the wavelengths used in such IR sensors may facilitate measurement of the partial pressure of a target gas in a gas sample such as may be obtained from a subject in a clinical setting or in an environmental monitoring application.

In capnography, such IR sensors may be used to measure the partial pressure (and hence the concentration) of carbon dioxide in gas exhaled by a subject during their respiratory cycle. Such carbon dioxide measurements may be indicative of a health status of a subject and may be used in various clinical and emergency scenarios. Certain clinical and emergency scenarios may demand rapid and accurate measurement of a subject's carbon dioxide profile during their respiratory cycle. There may be scenarios where such measurements need to be acquired within a broad ambient temperature range, as may be encountered in different clinical scenarios.

In some examples, a source of IR radiation in some IR sensors may comprise an electrically-powered broadband IR radiation source such as an incandescent lamp or a gas discharge lamp. In some examples, two or more IR detectors may be used to measure absorption, by the target gas constituent in a gas sample region, of the IR radiation at different wavelengths. The signals produced by the IR detectors may be indicative of the partial pressure of a target gas.

However, the spectral power of IR radiation output by the IR source and the spectral responsivity of the IR detectors can vary due to various factors such as a change in ambient temperature. Certain techniques may be used to reduce the effect of such factors on the accuracy of the measurements used to determine the partial pressure of the target gas. For example, the IR source(s) may be appropriately controlled by supplying electrical power at an appropriate rate to ensure that the spectral output power and system temperature is maintained within an acceptable range. In another example, the IR detectors may be subject to temperature control (e.g., by heating and/or cooling) to ensure that the spectral responsivity of the IR detectors is maintained within an acceptable range. In another example, the IR source and/or IR detectors may be recalibrated when needed such as when the ambient temperature drifts outside an acceptable range. In another example, measurements acquired by the IR detectors may be compensated based on an analysis of previously-obtained measurements. The implementation of such control and/or compensation may be associated with trade-offs in terms of power consumption, number of components used, size, weight, cost, complexity and/or functionality of the IR sensor.

SUMMARY OF THE INVENTION

Aspects or embodiments described herein may relate to improving the implementation and/or deployment of apparatus, methods and systems for gas sensing. Aspects or embodiments described herein may obviate one or more problems associated with gas sensing in different scenarios and/or hardware used for such gas sensing.

In a first aspect of the invention, an apparatus is described.

The apparatus comprises an infrared, IR, generating system. The IR generating system comprises a first IR source configured to produce IR radiation for forming a first IR beam in a first spectral band. The IR generating system further comprises a second IR source configured to produce IR radiation for forming a second IR beam in a second spectral band. The first spectral band is associated with a first attenuation coefficient of a target gas. The second spectral band is associated with a second attenuation coefficient of the target gas. The second attenuation coefficient is higher than the first attenuation coefficient. An intensity of the IR radiation produced by the first IR source is modulatable in time in response to modulation of power for operating the first IR source. An intensity of the IR radiation produced by the second IR source is modulatable in time in response to modulation of power for operating the second IR source. The intensity of the IR radiation produced by the first IR source is modulatable independently of the intensity of the IR radiation produced by the second IR source.

The apparatus further comprises a beam manipulation system. The beam manipulation system is configured to combine a beam path of the first and second IR beams and direct the first and second IR beams along the beam path through a gas sample region.

The apparatus further comprises an IR detection system. The IR detection system is configured to detect an intensity of the first and second IR beams after passage through the gas sample region. The IR detection system is configured to produce a signal. The signal is indicative of the detected intensity due to the first IR beam, wherein a first parameter derived from a first time interval of the signal is indicative of a level of attenuation of the first IR beam in the gas sample region. The signal is further indicative of the detected intensity due to the second IR beam, wherein a second parameter derived from a second time interval of the signal is indicative of a level of attenuation of the second IR beam in the gas sample region. A comparison between the second parameter and the first parameter is indicative of a concentration of the target gas in the gas sample region.

Some embodiments relating to the first and other aspects are described below.

In some embodiments, the target gas is at least one constituent of gas for inhalation by a subject and/or at least one constituent of gas exhaled by the subject. The apparatus may be configured to obtain an indication of the concentration of the at least one constituent in a gas sample obtained from the gas for inhalation by the subject and/or the gas exhaled by the subject.

In some embodiments, the signal comprises a convolution of a first signal component corresponding to the detected intensity due to the first IR beam and a second signal component corresponding to the detected intensity due to the second IR beam. The first parameter may be derivable from the signal based on a deconvolution of first and second signal components in the first time interval. The second parameter may be derivable from the signal based on a deconvolution of first and second signal components in the second time interval.

In some embodiments, the intensity of the IR radiation produced by the first and second IR sources is modulatable such that the intensity of the IR radiation produced by the first IR source is modulated at the same frequency as, but out of phase with, the intensity of the IR radiation produced by the second IR source.

In some embodiments, the intensity of the IR radiation produced by the first and second IR sources is modulatable such that the intensity of the IR radiation produced by the first IR source is modulated at a different frequency to the intensity of the IR radiation produced by the second IR source.

In some embodiments, the intensity of the IR radiation produced by the first and second IR sources is modulatable such that the intensity of the IR radiation produced by the first IR source has a higher intensity than the IR radiation produced by the second IR source during the first time interval.

In some embodiments, the intensity of the IR radiation produced by the first and second IR sources is modulatable such that the intensity of the IR radiation produced by the second IR source has a higher intensity than the IR radiation produced by the first IR source during the second time interval.

In some embodiments, the intensity of the IR radiation produced by the first and second IR sources is modulatable such that the IR radiation produced by the second IR source is produced continuously or repeatedly over a period of time. The signal produced by the IR detection system over the period of time may be indicative of a plurality of values for the second parameter. The plurality of values for the second parameter may be indicative of the level of attenuation of the second IR beam in the gas sample region over the period of time. The plurality of values for the second parameter may be indicative of any variation of the concentration of the target gas over the period of time.

In some embodiments, the intensity of the IR radiation produced by the first and second IR sources is modulatable such that the IR radiation produced by the first IR source is produced at least once before, during and/or after the period of time. The signal produced by the IR detection system at least once before, during and/or after the period of time may be indicative of at least one value for the first parameter. The at least one value for the first parameter may be indicative of the level of attenuation of the first IR beam in the gas sample region.

In some embodiments, the period of time corresponds to a phase of a respiratory cycle.

In some embodiments, the beam manipulation system is configured to combine the beam path of the first and second IR beams through the gas sample region such that an optical axis of the first and second IR beams is collinear in the gas sample region.

In some embodiments, the apparatus further comprises a control system for modulating the power for operating the first and second IR sources to independently modulate the intensity of the IR radiation produced by the first IR source and the intensity of the IR radiation produced by the second IR source.

In some embodiments, the control system is configured to, in response to receiving an indication of whether the first and/or second parameter is to be determined, modulate the intensity of the IR radiation produced by the first IR source and the intensity of the IR radiation produced by the second IR source such that the IR detection system produces the signal indicative of the first and/or second parameter.

In some embodiments, the apparatus further comprises a processing system configured to derive the first and second parameters from the signal and/or perform the comparison between the second parameter and the first parameter to obtain an indication of the concentration of the target gas in the gas sample region.

In some embodiments, the processing system is configured to determine the first parameter from the signal based on a range of signal values obtained during the first time interval.

In some embodiments, the processing system is configured to determine the second parameter from the signal based on a range of signal values obtained during the second time interval.

In some embodiments, the processing system is configured to deconvolve a first signal component corresponding to the detected intensity due to the first IR beam from a second signal component corresponding to the detected intensity due to the second IR beam based on an indicated timing of the modulated intensity of the IR radiation produced by the first IR source and the modulated intensity of the IR radiation produced by the second IR source. The processing system may be further configured to derive the first parameter from the first signal component and derive the second parameter from the second signal component.

In some embodiments, the IR detection system comprises an IR detector comprising an IR-sensitive detection area positioned to detect both the first and second IR beams using the same detection area.

In some embodiments, the IR generating system further comprises a third IR source configured to produce IR radiation for forming a third IR beam in a third spectral band. The third spectral band may be associated with a third attenuation coefficient of a second target gas. The third attenuation coefficient may be higher than the first attenuation coefficient. An intensity of the IR radiation produced by the third IR source may be modulatable in time in response to modulation of power for operating the third IR source. The intensity of the IR radiation produced by the third source may be modulatable independently of the intensity of the IR radiation produced by the first and second IR sources. The beam manipulation system may be configured to combine a beam path of the first, second and third IR beams and direct the first, second and third IR beams along the beam path through the gas sample region. The IR detection system may be configured to detect an intensity of the first, second and third IR beams after passage through the gas sample region. The signal produced by the IR detection system may be further indicative of the detected intensity due to the third IR beam. A third parameter derived from a third time interval of the signal may be indicative of a level of attenuation of the third IR beam in the gas sample region. A comparison between the third parameter and the first parameter may be indicative of a concentration of the second target gas in the gas sample region.

In a second aspect of the invention, a respiratory monitoring system is described. The respiratory monitoring system comprises a respiratory gas sampling system. The respiratory gas sampling system is configured to obtain a respiratory gas sample. The respiratory monitoring system further comprises an apparatus according to the first aspect or any related embodiment. The respiratory gas sampling system is configured to provide the obtained respiratory gas sample in the gas sample region of the apparatus. The apparatus is further configured to produce an indication of the concentration of the target gas in the obtained respiratory gas sample.

In a third aspect of the invention, a method is described.

The method comprises producing, using a first IR source, IR radiation for forming a first IR beam in a first spectral band.

The method further comprises producing, using a second IR source, a second IR beam in a second spectral band, The first spectral band is associated with a first attenuation coefficient of a target gas. The second spectral band is associated with a second attenuation coefficient of the target gas. The second attenuation coefficient is higher than the first attenuation coefficient. An intensity of the IR radiation produced by the first IR source is modulatable in time in response to modulation of power for operating the first IR source. An intensity of the IR radiation produced by the second IR source is modulatable in time in response to modulation of power for operating the second IR source. The intensity of the IR radiation produced by the first IR source is modulatable independently of the intensity of the IR radiation produced by the second IR source.

The method further comprises combining, using a beam manipulation system, a beam path of the first and second IR beams to direct the first and second IR beams along the beam path through a gas sample region.

The method further comprises detecting, using an IR detection system, an intensity of the first and second IR beams after passage through the gas sample region.

The method further comprises producing, using the IR detection system, a signal. The signal is indicative of the detected intensity due to the first IR beam. A first parameter derived from a first time interval of the signal is indicative of a level of attenuation of the first IR beam in the gas sample region. The signal is further indicative of the detected intensity due to the second IR beam. A second parameter derived from a second time interval of the signal is indicative of a level of attenuation of the second IR beam in the gas sample region. A comparison between the second parameter and the first parameter is indicative of a concentration of the target gas in the gas sample region.

According to certain embodiments described herein, at least two independently modulated IR beams may be multiplexed by combining the IR beams to facilitate measurement of attenuation of the IR beams by a target gas with reduced or minimal temperature dependence. Certain embodiments may allow a signal from an IR detection system for detecting the intensity of at least two IR beams to be de-multiplexed based on a synchronization with the IR radiation output profile of each IR source (e.g., based on a model of the IR source resistance and/or knowledge of the type of IR source). Certain embodiments may enable the fast and/or accurate signal de-multiplexing from the IR detection system. Certain embodiments may provide apparatus that can operate at relatively low power (e.g., due to reduced number of components and/or independent modulation of the IR sources) in a compact and/or robust package while also providing accurate measurements over a relatively broad ambient temperature range. Certain embodiments may be deployed for multi-gas sensing applications. Certain embodiments refer to apparatus that may be deployable in a range of scenarios such as clinical and/or emergency scenarios while still providing rapid and accurate measurements (e.g., for capnography applications).

These and other aspects of the invention will be apparent from and elucidated with reference to the embodiment(s) described hereinafter.

BRIEF DESCRIPTION OF DRAWINGS

Exemplary embodiments of the invention will now be described, by way of example only, with reference to the following drawings, in which.

DETAILED DESCRIPTION OF THE EMBODIMENTS

Figure 1:
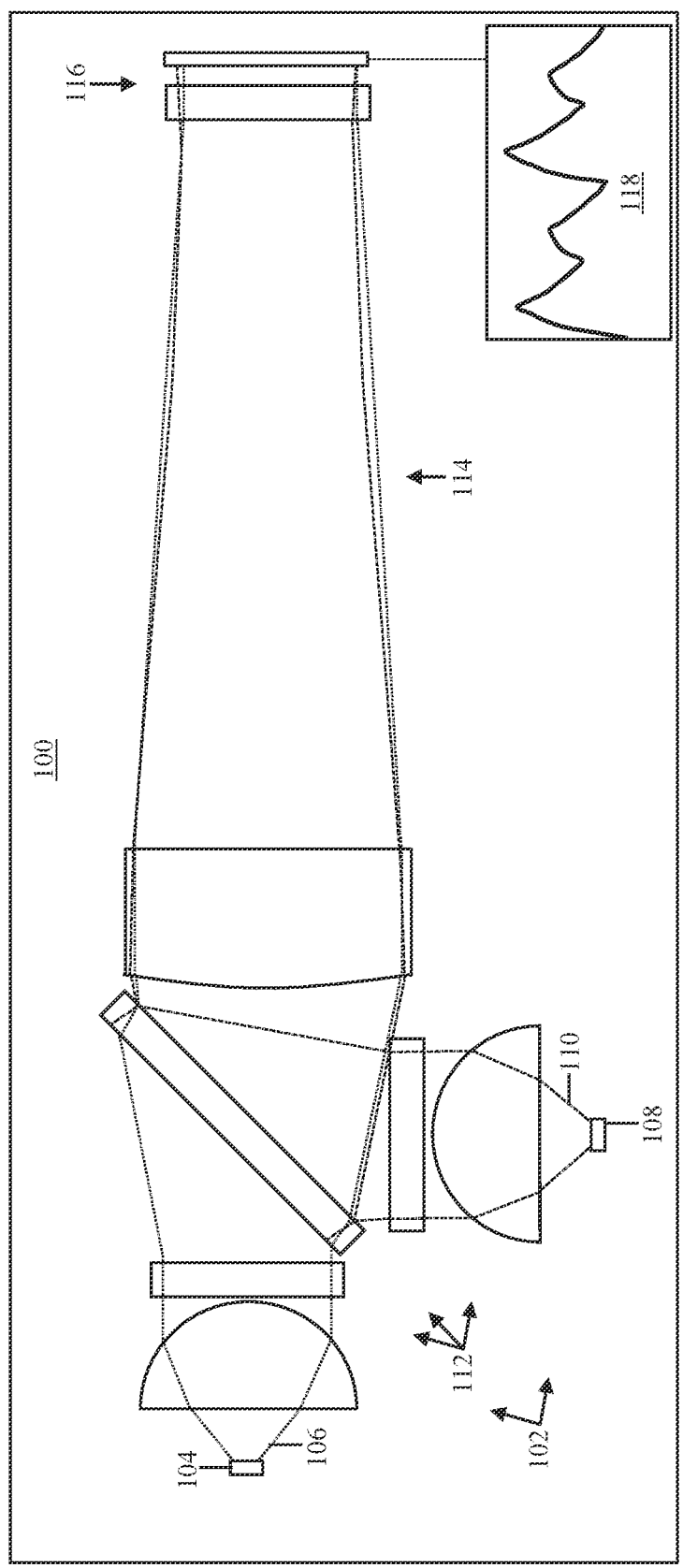
FIG. 1 is a schematic drawing of an apparatus for gas sensing according to an embodiment.

As referred to above, a change in ambient temperature may affect the operation of IR sources and/or IR detectors such as used in certain gas sensing applications. In some cases, a change in ambient temperature may lead to inaccurate measurements of IR absorption by a target gas, which may lead to an erroneous estimation of the partial pressure (and hence concentration) of a target gas in a gas sample. Although some applications may tolerate a certain level of inaccuracy for some measurements, certain applications such as capnography may need the measurements to have been obtained with acceptable accuracy.

An example way to reduce the risk of obtaining inaccurate measurements of the partial pressure of a gas is to control the operating temperature of components such as IR sources and/or IR detectors.

For example, an electrically-powered IR source may be supplied with electrical power which may, in some cases, be modulated in order for temperature of the IR source to be maintained within an acceptable range. In the case that the IR source is an incandescent lamp, appropriate modulation of the electrical power supplied to the IR source may prevent overheating and/or underheating such that the spectral power (i.e., power output at each part of the emitted spectrum) of the IR source remains within an acceptable range. In the case that the IR source is a gas discharge lamp, appropriate modulation of the electrical power supplied to the lamp may provide control over the spectral power output of the lamp. Other types of electrically-powered IR sources include solid-state (i.e., semiconductor-based) IR emitters such as IR light emitting diodes (LEDs) or laser diodes. The relationship between the spectral power output (and other performance characteristics) of these different types of IR sources may be affected by the temperature at which the IR source is operating, which may depend on both the ambient temperature and self-heating due to the operation of the IR source.

As highlighted above, control (e.g., temperature control by heating or cooling) may be used to control the performance (e.g., spectral power) of an IR source. However, such control may require additional hardware (e.g., for electrical power supply modulation, dedicated cooling equipment, thermoelectric cooling, heating, temperature measurement, etc.) that may add to the power consumption, number of components used, size, weight, cost, complexity and/or functionality of an IR sensor that implements temperature control.

Although the spectral responsivity of some IR detectors may not be significantly affected by temperature variations as experienced in some scenarios, the spectral responsivity of some other IR detectors may be more significantly affected by temperature variations to such an extent that measurements by such IR detectors may be erroneous. In some cases, this temperature sensitivity may depend on how the IR detectors are being operated as well as the type of IR detector being used. By way of example, lead selenide (PbSe)-based IR detectors and/or indium arsenide antimonide (InAsSb)-based IR detectors may exhibit good responsivity in the wavelength range 2 to 5 microns. However, such materials may be highly temperature sensitive in that the responsivity at a certain wavelength changes by a large factor within the temperature operating range of the IR detector. For example, responsivity may change by a factor of 8 (eight) for an ambient temperature change from 0° C. to 60° C., which is an example of a plausible ambient temperature range within which an IR sensor may be used in capnography.

As already mentioned, additional hardware may be provided for maintaining a constant temperature for such an IR sensor. However, such additional hardware involves trade-offs such as using additional power and a wait time to reach a specified temperature. The trade-offs between power consumption, time to accuracy and the temperature swing may be problematic for clinical and emergency applications, where fast and accurate measurements may be needed.

As also highlighted in an example above, re-calibration (e.g., periodically or whenever a change in temperature exceeds a pre-determined threshold) of hardware settings may be used to reduce error in measurements. In another example, compensation techniques may be applied to newly-obtained measurements based on analysis of previously-obtained measurements (e.g., within a range of different temperatures) to take into account factors that affect measurements such as a change in temperature (e.g., based on application of the ideal gas law).

Although it may be possible to calibrate and/or compensate for the IR detector temperature sensitivity, this process may be difficult for an end-user to implement and/or may not necessarily yield sufficiently accurate measurements in various deployment scenarios (e.g., where the ambient temperature may vary) where such calibrations and/or compensations are based on different deployment scenarios (e.g., where the calibration/compensation measurements were obtained at a certain ambient temperature range).

Certain embodiments described herein may facilitate deployment and/or implementation of gas sensing in various scenarios. Certain embodiments described herein may reduce the need for additional components in an IR sensor used for gas sensing. Certain embodiments described herein may reduce the need for calibration of such an IR sensor and/or reduce or avoid the need to compensate for various factors that may otherwise affect the accuracy and/or reliability of such an IR sensor.

FIG. 1 is a schematic drawing of an apparatus 100 for gas sensing according to an embodiment. The apparatus 100 may implement the functionality of an IR sensor and may be deployed in various scenarios where gas sensing is needed. For example, the apparatus 100 may be used for gas sensing in a clinical scenario (e.g., for the measurement of the partial pressure/concentration of carbon dioxide and/or other target gases of interest such as anesthetic gases such as nitrous oxide). In another example, the apparatus 100 may be used in an environmental monitoring application.

The apparatus comprises an infrared, IR, generating system 102.

The IR generating system 102 comprises a first IR source 104. The first IR source 104 is configured to produce IR radiation for forming a first IR beam 106 in a first spectral band.

The IR generating system 102 further comprises a second IR source 108. The second IR source 108 is configured to produce IR radiation for forming a second IR beam 110 in a second spectral band.

The manner by which the IR radiation is produced and how the respective IR beams 106, 110 are formed may depend on the type of IR source 104, 108 and/or how the IR radiation is provided in the first and second spectral bands. Certain embodiments described below provide further details on the implementation of IR sources 104, 108 and how the respective IR beams 106, 110 may be formed.

Some further details of the implementation of the apparatus 100 according to the present embodiment are described below.

A first part of the implementation is now described and refers to the attenuation of the first and second spectral bands due to a target gas.

According to the first part of the implementation, the first spectral band is associated with a first attenuation coefficient of a target gas. Further, the second spectral band is associated with a second attenuation coefficient of the target gas. Further, the second attenuation coefficient is higher than the first attenuation coefficient.

An attenuation coefficient of the target gas refers to the proportion of IR radiation that is absorbed, scattered and/or otherwise attenuated by the target gas. As referred to above, there is a first and second spectral band, each of which is associated with first and second attenuation coefficients, respectively. Thus, the level of attenuation may be different for each of the first and second spectral bands. In particular, IR radiation in the second spectral band (i.e., of the second IR beam) is attenuated more by the target gas than IR radiation in the first spectral band (i.e., of the first IR beam).

With reference to the examples given above in relation to the absorption bands of carbon dioxide, if the target gas is carbon dioxide, the first spectral band may include wavelengths that do not include an absorption peak wavelength of carbon dioxide (so the first spectral band is associated with a 'first attenuation coefficient') such as 4.3 microns ($\mu m$) (i.e., the first spectral band may not comprise or may not substantially overlap this wavelength or other wavelength(s) associated with absorption by carbon dioxide).

The second spectral band may include wavelengths that do include an (e.g., at least one) absorption peak wavelength of carbon dioxide (so the second spectral band is associated with a 'second attenuation coefficient') such as 4.3 $\mu m$ (i.e., the second spectral band comprises or substantially overlaps this wavelength or other wavelength(s) associated with absorption by carbon dioxide).

Since the attenuation coefficient associated with the second spectral band is higher than the attenuation coefficient associated with the first spectral band, if IR radiation in the second spectral band is attenuated (after passing through a gas sample) more so than IR radiation in the first spectral band, this may be indicative of the target gas being present in a measured sample of gas. However, if IR radiation in the second spectral band is attenuated (or not attenuated) to the same extent as IR radiation in the first spectral band, this may be indicative of there being no or little target gas being present in the gas sample.

A second part of the implementation is now described and refers to the modulation of the intensity of the IR radiation.

According to the second part of the implementation, an intensity of the IR radiation produced by the first IR source 104 is modulatable in time (i.e., the intensity can be modulated in time) in response to modulation of power for operating the first IR source 104. Further, an intensity of the IR radiation produced by the second IR source 108 is modulatable in time in response to modulation of power for operating the second IR source 108. Further, the intensity of the IR radiation produced by the first IR source 104 is modulatable independently of the intensity of the IR radiation produced by the second IR source 108.

Thus, the first IR source 104 can be operated independently of the second IR source 108 such that the intensity of the first and second IR beams 106, 110 can be modulated in time as and when needed, as is explained in more detail below.

Further details of the apparatus 100 are described below.

The apparatus 100 further comprises a beam manipulation system 112. The beam manipulation system 112 is configured to combine a beam path of the first and second IR beams 106, 110 and direct the first and second IR beams 106, 110 along the beam path through a gas sample region 114.

In some cases, the first and second IR beams 106, 110 may not be produced at the same time (since the intensity of the IR beams 106, 110 may be modulated in time). Thus, the beam manipulation system 112 may combine the two IR beams 106, 110 such that they may be directed along substantially the same beam path (e.g., comprising the gas sample region 114) but this may not necessarily result in the two IR beams 106, 110 being directed along the beam path at the same time (unless there is an overlap in time when both the first and second IR sources 104, 108 are producing IR radiation). The beam path of the first and second IR beams 106, 110 may be the same or at least substantially similar (e.g., at least a portion of the beam path of first and second IR beams 106, 110 may follow substantially the same beam path in the gas sample region). Further details of the beam manipulation system 112 and the gas sample region 114 are described in more detail in relation to certain embodiments described below.

The apparatus 100 further comprises an IR detection system 116. The IR detection system 116 is configured to detect an intensity of the first and second IR beams 106, 110 after passage through the gas sample region 114. The IR detection system 116 is configured to produce a signal 118 (e.g., an electrical signal) indicative of certain information about the target gas as detailed below.

The signal 118 is indicative of the detected intensity due to the first IR beam 106. A first parameter (such as an amplitude and/or difference between peak/maximum and trough/minimum intensity values) derived from a first time interval of the signal 118 is indicative of a level of attenuation of the first IR beam 106 in the gas sample region 114. In some cases, the start and end points of the first time interval correspond to intensity values used to calculate the first parameter. For example, a trough/minimum intensity value may be observed at the start point and a peak/maximum intensity value may be observed at the end point of the first time interval. The first parameter may be indicative of the attenuation of the first IR beam 106 in the gas sample region 114. In an example, the difference between the two intensity values described above may be proportional to attenuation of the first IR beam 106 in the gas sample region 114.

The signal 118 is also indicative of the detected intensity due to the second IR beam 110. A second parameter derived from a second time interval of the signal 118 is indicative of a level of attenuation of the second IR beam 110 in the gas sample region 114. The second parameter may be derived from the second time interval in the same way as the first parameter may be derived from the first time interval. The second parameter may be indicative of the attenuation of the second IR beam 110 in the gas sample region 114. In an example, the difference between peak and trough intensity values derived from the second time interval may be proportional to attenuation of the second IR beam 110 in the gas sample region 114.

The first and second time intervals may be the same length of time or a different length of time. The first and second time intervals may at least partially overlap or not overlap at all. If the first and second time intervals completely overlap, it may be difficult to extract the first and/or second parameters within the overlapping time interval (although it may be easier to extract the first and/or second parameters in a different time interval). However, if the first and second time intervals partially overlap or do not overlap, it may be relatively straightforward to extract the first and/or second parameters.

A comparison between the second parameter and the first parameter is indicative of a concentration (or partial pressure) of the target gas in the gas sample region 114. Since the attenuation of the second IR beam 110 may be due to the presence of the target gas in the gas sample region 114 (e.g., since the second spectral band is associated with the higher attenuation coefficient associated with the target gas) and the attenuation of the first IR beam 106 may not be due to the presence of the target gas, a comparison of the first and second parameters may be indicative of the concentration of the target gas. Certain embodiments described below refer to how the comparison may be made.

Thus, the signal 118 produced by the apparatus 100 may be used to estimate or determine a change in the concentration (or partial pressure) of the target gas within the gas sample region 114. This change in concentration may be used to infer the actual concentration of the target gas. As referred to above, determining the concentration of the target gas may be useful in various applications such as capnography or environmental monitoring.

Thus, the apparatus 100 may facilitate time and wavelength multiplexing of the IR radiation produced by the first and second IR sources 104, 108. The first and second spectral bands may be selected to have different (and potentially narrowband) wavelengths for allowing independent modulation and/or power-efficient operation of each channel associated with the first and second IR beams 106, 110.

In some cases, such multiplexing may facilitate independent modulation of the intensity of the IR radiation produced by the first and second IR sources 104, 108. Each IR channel (i.e., a first channel associated with the first IR beam 106 and a second channel associated with the second IR beam 110) may be monitored independently and with the same IR detection system 116. In some cases, such a set-up may facilitate a power-efficient operation by only causing the first and second IR sources 104, 108 to produce IR radiation when needed. The multiplexed set-up may also avoid the need to use additional components for detecting the intensity of both the first and second IR beams e.g., at the same time. Instead, the IR detection system 116 may be configured to detect the intensity of the first and second IR beams 106, 110 as and when the first and second IR sources 104, 108 produce IR radiation for forming the first and second IR beams 106, 110. The multiplexed set-up may facilitate a flexible operation of the apparatus 100 such that certain components such as the first and second IR sources 104, 108 may be used when needed.

In some cases, the apparatus 100 may operate to produce accurate measurements of the intensity of the first and second IR beams 106, 110 with reduced or minimal delay after start-up (e.g., for an apparatus 100 that is ready for use when needed). Use of independently modulated first and second IR beams 106, 110 may facilitate measurement of the concentration of the target gas that is independent of the ambient temperature since the measurement of the intensity of the first IR beam 106 after passage through the gas sample region 114 may act as a 'reference' signal representative of attenuation that is not due to the target gas. The 'comparison' may allow the effect of such other factors (e.g., temperature variations, scattering particles, etc., that may cause attenuation of both the first and second IR beams 106, 110) to be taken into account so that the measurement of the intensity of the second IR beam 110 is representative of attenuation by the target gas (and not any other constituent gas or component of the gas sample).

In some cases, the production of IR radiation by the first and second IR sources 104, 108 may be monitored (e.g., based on a measurement of the IR source 104, 108 electrical resistance being indicative of the intensity level of the IR radiation produced by the IR sources 104, 108). As explained in more detail below, such monitoring of the first and second IR sources 104, 108 may be useful for de-coupling the signal 118 due to the first IR beam 106 (after attenuation, if any attenuation occurs) from the signal 118 due to the second IR beam 110 (after attenuation due to the presence of the target gas).

Thus, the independent operation and modulation of the first and second IR sources 104, 108 may be useful for allowing the effect of certain factors (e.g., temperature variations, scattering particles, etc.) to be taken into account to obtain a representative, rapid and accurate indicative measure of the concentration of the target gas. Further, the independent operation and modulation of the first and second IR sources 104, 108 may be useful for de-coupling the two channels associated with the first and second IR sources 104, 108 and establishing the contribution due to each channel, and hence may facilitate a representative, rapid and accurate indicative measure of the concentration of the target gas.

In some cases, the apparatus 100 may be operated under an extended ambient temperature range, which may be useful for deploying the apparatus 100 in various scenarios (e.g., clinical and/or emergency scenarios), while ensuring the accuracy of measurements for allowing the concentration of the target gas to be indicated with a certain level of confidence.

In some cases, the design of the apparatus 100 is such that the apparatus 100 can have a relatively compact size, low weight, simple optical architecture, simple design (due to avoiding use of certain components which may otherwise increase the size of the apparatus 100), and/or is energy efficient (e.g., due to independent operation of the first and second IR sources 104, 108 and using the same IR detection system 116 for detecting the intensity of the first and second IR beams 106, 110). In some cases, the apparatus 100 may be portable/wearable due to its compact size and potential compatibility with battery-powered operation.

Thus, the apparatus 100 may be deployable in various scenarios and may be capable of providing an accurate indication of the concentration of the target gas in such scenarios.

Figure 2:
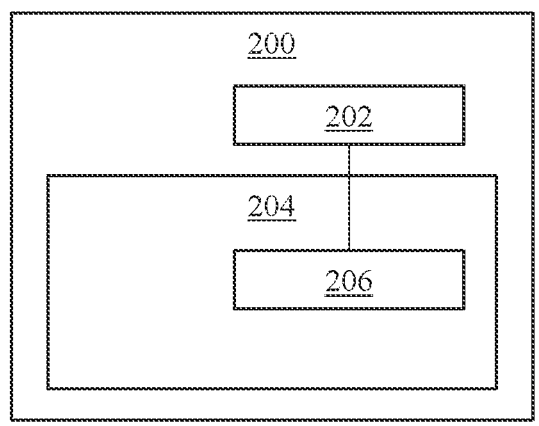
FIG. 2 is a schematic drawing of a system for gas sensing according to an embodiment.

FIG. 2 is a schematic drawing of a respiratory monitoring system 200 for respiratory gas sensing according to an embodiment. The respiratory monitoring system 200 comprises a respiratory gas sampling system 202. In this embodiment, the respiratory gas sampling system 202 is configured to obtain a respiratory gas sample, which may include gas that is inhaled (e.g., oxygen, anesthetic gas, etc.) and/or exhaled (e.g., carbon dioxide, water vapor) by a subject such as a patient. For example, the respiratory gas sampling system 202 may be part of a ventilator (not shown) or otherwise deployed for respiratory monitoring purposes. The respiratory gas sampling system 202 may comprise infrastructure (not shown) such as tubing, removable sample chamber, etc., for acquiring a gas sample from the inhaled and/or exhaled gas.

The respiratory monitoring system 200 further comprises an apparatus 204 according to any embodiment described herein, for example, apparatus 100 or certain other apparatus described below. With reference to the apparatus 100 of FIG. 1, the respiratory gas sampling system 202 is configured to provide the obtained respiratory gas sample in the gas sample region 206 (i.e., the gas sample region 114 of FIG. 1) of the apparatus 204. The apparatus 100 is configured to produce an indication (e.g., via the signal 118) of the concentration of the target gas in the obtained respiratory gas sample. In some cases, the gas sample may be passed through the gas sample region 206 (e.g., repeatedly or when needed). In this case, the gas sample region 206 may have a gas inlet and outlet (not shown) to allow the gas sample to flow through the gas sample region 206. In some cases, the gas sample may be stored in a sample chamber (not shown) that is positionable in the gas sample region 206 when needed (i.e., the sample chamber may be replaced whenever a gas sample is obtained).

Figure 3:
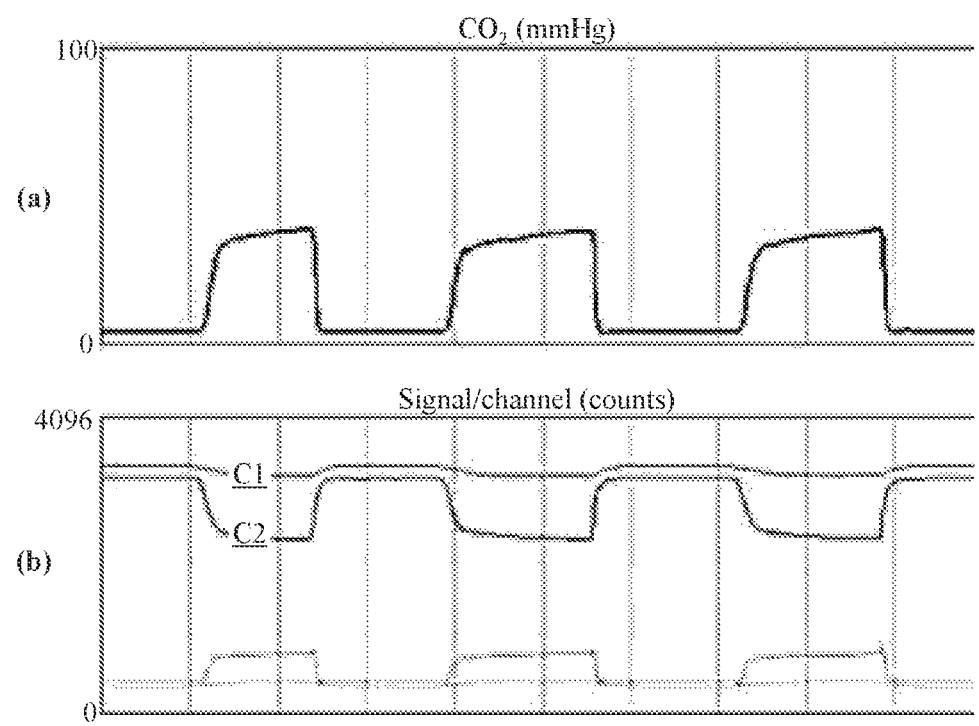
FIG. 3 shows graphs depicting data representative of the sensed concentration of carbon dioxide during a respiratory cycle.

FIG. 3 shows graphs depicting data representative of the sensed concentration of carbon dioxide during a respiratory cycle.

Graph (a) is a capnogram representing the partial pressure (in millimeters of mercury, mmHg) of carbon dioxide ($CO_2$) in a respiratory gas sample taken over three respiratory cycles. The capnogram indicates the level of carbon dioxide in the gas sample during inhalation and exhalation. The profile of the capnogram may be indicative of the health status of the subject. For example, the profile of the capnogram may be indicative of certain health issues.

Graph (b) shows the de-coupled channels (C1, C2) derived from the signal 118. The de-coupling of the channels is described in more detail below. The first channel C1 refers to the detected intensity of the first IR beam 106 after passing through the gas sample region 114. The second channel C2 refers to the detected intensity of the second IR beam 110 after passing through the gas sample region 114. As depicted by graph (b), there is not much variation in the intensity of the first IR beam 106 (represented by channel C1) over time because the IR radiation in the first spectral band is used for reference purposes and is not substantially attenuated by the presence of carbon dioxide (the concentration of which varies over time during the respiratory cycle). However, the variation in the concentration of the carbon dioxide leads to attenuation of the second IR beam 110 (represented by second channel C2) over time since the attenuation coefficient associated with the second spectral band is higher than the attenuation coefficient associated with the first spectral band. A comparison (such as a difference or ratiometric calculation) between the channels, C1 and C2, may be used to produce the capnogram of graph (a).

Figure 4:
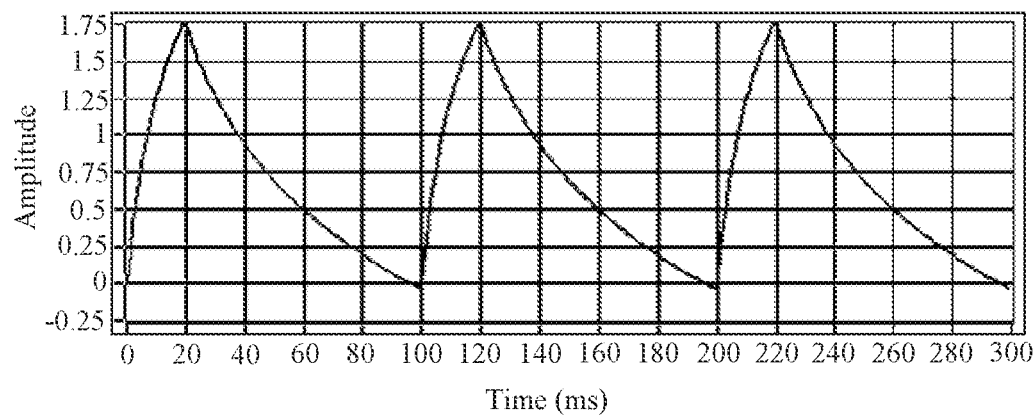
FIG. 4 is a graph depicting data representative of the absorption of IR radiation in a first spectral band, as detected by a single IR detector channel.

FIG. 4 is a graph depicting data representative of the attenuation of IR radiation (if any such absorption occurs) in a first spectral band, as detected by a single IR detector channel. In this case, IR radiation produced by the single IR source is modulated by supplying electrical power to the IR source. As depicted by the graph, the detected intensity increases (when electrical power is supplied or increased) and then decreases (when electrical power is not supplied or is reduced) periodically. The profile of the detected intensity shown by the graph may be representative of the type of IR source. For example, an incandescent lamp may continue to produce IR radiation even when electrical power is no longer supplied due to the lamp being slow to cool down. Hence, the depicted reduction (downward slope) in detected IR radiation may be representative of the continued production of IR radiation by the IR source. With reference to FIGS. 1 and 3, FIG. 4 may represent the measured signal 118 that may be obtained by operating only the first channel C1.

Figure 5:
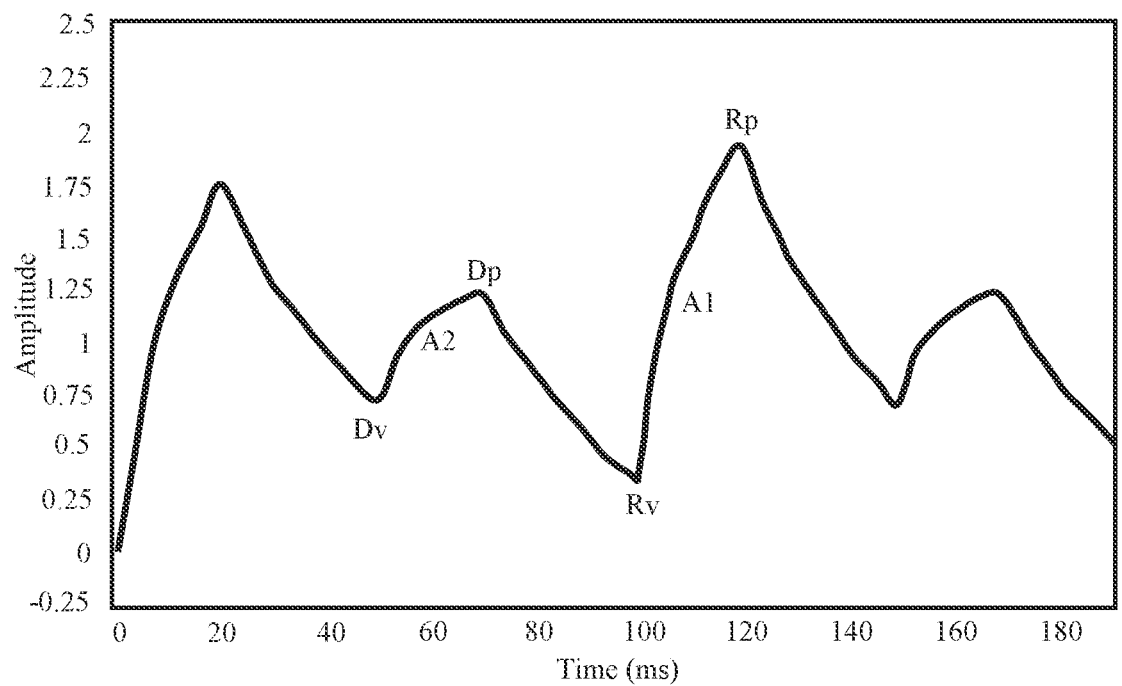
FIG. 5 is a graph depicting data representative of the absorption of IR radiation in a first and second spectral band, as detected by a single IR detector channel, according to an embodiment.

FIG. 5 is a graph depicting data representative of the attenuation of IR radiation in both a first and second spectral band, as detected by a single IR detector channel (such as depicted by the apparatus 100), according to an embodiment. Reference is made to features and functionality of the apparatus 100. In this case, the modulation of the first and second IR sources is out of phase so that the first IR source 104 is supplied with power such that peak IR emission occurs at around 20 milliseconds (ms) and 120 ms (in correspondence with the example depicted by FIG. 4) and so that the second IR source 108 is supplied with power such that peak IR emission occurs at around 70 ms and 170 ms. In other words, FIG. 5 shows the addition of the second channel C2 to the data shown by FIG. 4. Thus, the contribution due to both the first and second channels C1 and C2 is depicted in the graph of FIG. 5. As shown by the graph, the second channel C2 registers a lower peak intensity than the first channel C1. This is because the second IR beam 110 may have experienced a greater level of attenuation (due to presence of the target gas) than the first IR beam 106. The data shown by FIG. 5 is an example of the 'raw' signal 118 that may be obtained by the IR detection system 116. This signal 118 may then be used to derive the channels C1 and C2 and associated capnogram shown by FIG. 3.

FIG. 5 also depicts the intensity values and time intervals that may be used to determine the first and second parameters.

The first parameter may be determined by calculating the difference (i.e., the amplitude, A1) between the peak/maximum intensity (Rp) and trough/minimum intensity (Rv). Thus the first time interval may refer to the time between which Rv and Rp are obtained (i.e., between 0 and 20 ms as well as between 100 and 120 ms in FIG. 5).

The second parameter may be determined by calculating the difference (i.e., the amplitude, A2) between the peak/maximum intensity (Dp) and trough/minimum intensity (Dv). Thus the second time interval may refer to the time between which Dv and Dp are obtained (i.e., between 50 and 70 ms as well as between 150 and 170 ms in FIG. 5).

It can be recognized that the amplitude, A1, associated with the first IR beam 106 (channel C1) is larger than the amplitude, A2, associated with the second IR beam 110 (channel C2). This is because the second IR beam 110 has been attenuated by the presence of the target gas in the gas sample region 114. The comparison between the amplitudes A1 and D2 (e.g., the difference or the ratiometric calculation A2/A1) may be indicative of the concentration of the target gas in the gas sample region 114.

Some embodiments relating to the apparatus 100 and other embodiments are described below. Any selected combination of the embodiments described below may be implemented by the apparatus 100 and other apparatus described below, where appropriate. Reference is made to the above figures in the description of the embodiments below.

In some embodiments, the target gas is at least one constituent of gas for inhalation by a subject and/or at least one constituent of gas exhaled by the subject. In this regard, the apparatus 100 is configured to obtain an indication of the concentration of the at least one constituent in a gas sample obtained from the gas for inhalation by the subject and/or the gas exhaled by the subject. Thus, in the case that the apparatus 100 is used for monitoring the gas inhaled and/or exhaled by a subject such as a patient, the apparatus 100 may be set-up to obtain the indication of the concentration of at least one selected target gas of interest (e.g., carbon dioxide, anesthetic gas, etc.).

In some embodiments, the signal 118 comprises a convolution of a first signal component corresponding to the detected intensity due to the first IR beam 106 and a second signal component corresponding to the detected intensity due to the second IR beam 110 (e.g., since the same IR detection system 116 is used to detect the intensity of both IR channels). The first parameter (e.g., 'A1') is derivable from the signal 118 based on a deconvolution of first and second signal components in the first time interval. The second parameter (e.g., 'A2') is derivable from the signal based on a deconvolution of first and second signal components in the second time interval.

The modulation of the first and second IR sources 104, 108 may be performed in various ways, as referred to in the embodiments described below. The choice of which modulation scheme to use may depend on, for example, the set-up of the apparatus 100 and/or whether measurements are needed to be obtained continually from one or both IR channels. Any combination of the modulation schemes may be implemented at the same time, where possible, or may be implemented at different times, where appropriate.

In some embodiments, the intensity of the IR radiation produced by the first and second IR sources 104, 108 is modulatable such that (i) the intensity of the IR radiation produced by the first IR source 104 is modulated at the same frequency as, but out of phase with, the intensity of the IR radiation produced by the second IR source 110. This embodiment is depicted by FIG. 5 where the peak output of the first and second IR sources 104, 108 is 180 degrees out of phase with each other. Other phase differences are possible such as 90 degrees (the choice of phase difference may be arbitrary). If the phase difference is 0 degrees within a particular time interval, it may be difficult to extract the first and second parameters although it may be easier to extract the first and second parameters in another time interval, as referred to below.

In some embodiments, the intensity of the IR radiation produced by the first and second IR sources 104, 108 is modulatable such that (ii) the intensity of the IR radiation produced by the first IR source 104 is modulated at a different frequency to the intensity of the IR radiation produced by the second IR source 108. In this case, the first and second channels, C1 and C2, corresponding to the output of the first and second IR sources 104, 108 may go in- and out-of-phase over a sampling time period. Thus, the indication of the concentration of the target gas may be obtained when possible over the sampling time period.

In some embodiments, the intensity of the IR radiation produced by the first and second IR sources 104, 108 is modulatable such that (iii) the intensity of the IR radiation produced by the first IR source has a higher intensity than the IR radiation produced by the second IR source during the first time interval. In some embodiments, the intensity of the IR radiation produced by the first and second IR sources 104, 108 is modulatable such that (iv) the intensity of the IR radiation produced by the second IR source has a higher intensity than the IR radiation produced by the first IR source during the second time interval. These embodiments are similar to the embodiment described above where there is phase difference in terms of the peak output of the first and second IR sources 104, 108.

Certain types of IR sources 104, 108 may continue emitting IR radiation even after electrical power is no longer supplied to the IR source 104, 108 (or if less electrical power is supplied in a particular time interval). Therefore, the first and second IR beams 106, 110 may both be 'on' at the same time if, in the 'first time interval', more power is supplied to the first IR source 104 than the second IR source 108 (or the second IR source 108 is not powered) such that peak IR output of the first IR source 104 occurs in the first time interval. Similarly, the first and second IR beams 106, 110 may both be 'on' at the same time if, in the 'second time interval', more power is supplied to the second IR source 108 than the first IR source 104 (or the first IR source 104 is not powered) such that peak IR output of the second IR source 108 occurs in the second time interval. As depicted by comparing FIGS. 4 and 5, emission of IR radiation by the first and second IR sources 104, 108 occurs at the same time such that there may be a contribution to the signal 118 due to both IR sources 104, 108 at the same time. However, since the peak intensity of the first IR beam 106 (e.g., time=20 ms) is out of phase with the peak intensity of the second IR beam 110 (e.g., time=70 ms), it may be possible to de-couple the effect of the on-going emission of IR radiation by the 'off or low power' IR source 104, 108 during each respective time interval. Certain types of IR sources may not produce IR radiation when powered-off (e.g., laser diodes), or the production of IR radiation may tail-off over a different timescale and/or at a different rate to that depicted by FIGS. 4 and 5.

In some embodiments, the intensity of the IR radiation produced by the first and second IR sources 104, 108 is modulatable such that (v) the IR radiation produced by the second IR source 108 is produced continuously or repeatedly over a period of time. The signal 118 produced by the IR detection system 116 over the period of time may be indicative of a plurality of values for the second parameter (e.g., 'A2'). The plurality of values for the second parameter may be indicative of the level of attenuation of the second IR beam 110 in the gas sample region 114 over the period of time. The plurality of values for the second parameter may be indicative of any variation of the concentration of the target gas over the period of time. In other words, in any period of time (e.g., comprising a plurality of 'second' time intervals), repeated measurements of the attenuation of the second IR beam 110 may be obtained.

In some embodiments, the intensity of the IR radiation produced by the first and second IR sources 104, 108 is modulatable such that (vi) the IR radiation produced by the first IR source 104 is produced at least once before, during and/or after the period of time. The signal 118 produced by the IR detection system 116 at least once before, during and/or after the period of time may be indicative of at least one value for the first parameter (e.g., 'A1'). The at least one value for the first parameter may be indicative of the level of attenuation of the first IR beam 106 in the gas sample region 114.

In other words, in the period of time over which the plurality of values for the second parameter are obtained (see embodiment (v)), at least one value for the first parameter may be obtained. Where the first parameter is indicative of a 'reference' level of attenuation and the second parameter is indicative of the concentration of the target gas, fewer measurements of the attenuation of the first IR beam 106 may be needed if it can be assumed that the reference level of attenuation does not change significantly over the period of time. Thus, in some cases, the first parameter need only be obtained when needed. An example scenario may be where the second IR source 108 is modulated at a frequency of 100 Hz (e.g., for obtaining the second parameter every 100 ms) and the first IR source 104 is modulated so that it produces IR radiation every 5 minutes (e.g., over a 100 ms time interval) so that a reference measurement of first parameter can be obtained. However, if more accuracy is needed, the values for the first parameter may be obtained more regularly such as the same number of times as the values for the second parameter within the period of time.

As highlighted above, a period of time may be defined over which to obtain a certain number of measurements. In some embodiments, the period of time corresponds to a phase of a respiratory cycle such as an inhalation phase, an exhalation phase or the full respiratory cycle of inhalation and exhalation. In an example, if the period of time is 5 seconds (as may be typical for the exhalation phase) and the modulation frequency is 100 ms, then 50 measurements may be obtained during this period of time. In an example, 1 measurement may be made using the first IR beam 106 and the remaining 49 measurements may be made using the second IR beam 110 (for 1 value of the first parameter and 49 values for the second parameter). In another example, 25 measurements may be made using the first IR beam 106 and the remaining 25 measurements may be made using the second IR beam 110 (for 25 values of the first parameter and 25 values for the second parameter).

Figure 6:
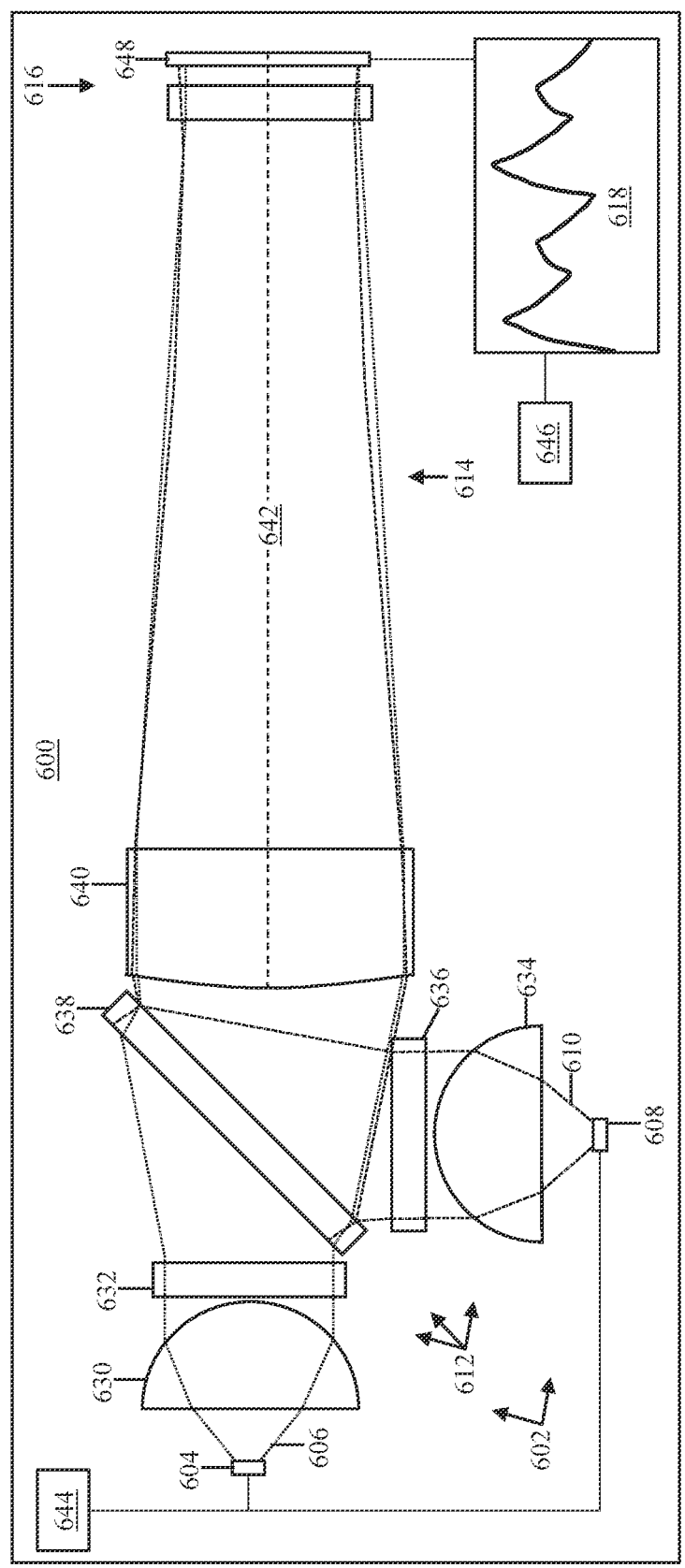
FIG. 6 is a schematic drawing of an apparatus for gas sensing according to an embodiment.

FIG. 6 is a schematic drawing of an apparatus 600 for gas sensing according to an embodiment. The apparatus 600 comprises features of the apparatus 100 of FIG. 1 and may be used for the same applications as described above. In this regard, such features of the apparatus 600 have reference signs incremented by 500 compared with FIG. 1. Various embodiments are described in relation to FIG. 6, which is used to assist in describing the features associated with these embodiments. Not all features may be present in certain variations of the apparatus 600. For example, features described in relation to any of the embodiments described below may be omitted in certain variations. In other words, FIG. 6 represents a possible combination of features for one variation of the apparatus 600. However, any selected combination of the features according to the embodiments described below may be provided in another variation of the apparatus 600.

Some details of the beam manipulation system 612 according to an embodiment are described below.

The beam manipulation system 612 comprises a first collector lens 630 configured to collect the first IR beam 606. The first collector lens 630 may collimate or at least reduce the divergence of the first IR beam 606. The beam manipulation system 612 further comprises a first filter 632 (e.g., a long-pass, band-pass or short-pass filter) to spectrally filter the IR radiation produced by the first IR source 604 (of the IR generating system 602) such that the first IR beam 606 has the 'first spectral content' after being filtered by the first filter 632.

The beam manipulation system 612 further comprises a second collector lens 634 configured to collect the second IR beam 610. The second collector lens 634 may collimate or at least reduce the divergence of the second IR beam 610. The beam manipulation system 612 further comprises a second filter 636 (e.g., a long-pass, band-pass or short-pass filter) to spectrally filter the IR radiation produced by the second IR source 608 (of the IR generating system 602) such that the second IR beam 610 has the 'second spectral content' after being filtered by the second filter 636.

In an example implementation of the apparatus 600, the second filter 636 is configured to pass IR radiation at around 4.3 microns, which is absorbed by carbon dioxide so that the detected intensity of the second IR beam 610 may be indicative of the concentration of carbon dioxide in the gas sample region 614. The first filter 632 may be configured to pass IR radiation at a different wavelength that does not absorb carbon dioxide to provide a reference measurement of the background attenuation (e.g., due to the presence of water vapor, scattering particles, etc.).

The beam manipulation system 612 further comprises a beam combiner 638 configured to transmit the first beam 606 and reflect the second IR beam 610 (or reflect the first beam 606 and transmit the second IR beam 610) such that the first and second IR beams 606, 610 are combined to have the same beam path (or substantially the same beam path). Due to the arrangement of the first and second IR sources 604, 608 with respect to the beam manipulation system 612, the first and second IR beams 606, 610 are directed along the same (or similar) beam path through the gas sample region 614.

In some embodiments, the beam manipulation system 612 further comprises a focusing lens 640 for focusing (or further collimating) the combined first and second IR beams 606, 610 onto the IR detection system 616, described in more detail below.

In some embodiments, the beam manipulation system 612 is configured to combine the beam path of the first and second IR beams 606, 610 through the gas sample region 614 such that an optical axis 642 of the first and second IR beams 606, 610 is collinear in the gas sample region 614. In other words, the first and second IR beams 606, 610 may have overlapping or substantially overlapping beam paths (with optical axes at 0 degrees, or just a few degrees, to each other) in the gas sample region 614.

The apparatus 600 further comprises a control system 644 for modulating the power (e.g., electrical power) for operating the first and second IR sources 604, 608 to independently modulate the intensity of the IR radiation produced by the first IR source 604 and the intensity of the IR radiation produced by the second IR source 608. The control system 644 may control the power supplied to the first and second IR sources 604, 608 via independent power supply lines, as depicted by FIG. 6. The control system 644 is depicted as being part of the apparatus 600 itself. In other embodiments, the functionality of the control system 644 may be implemented by at least one external device (not shown) such as independently-controllable external power supplies for each of the first and second IR sources 604, 608.

In some embodiments, the control system 644 is configured to, in response to receiving an indication of whether the first and/or second parameter is to be determined, modulate the intensity of the IR radiation produced by the first IR source 604 and the intensity of the IR radiation produced by the second IR source 608 such that the IR detection system produces the signal 618 indicative of the first and/or second parameter. Thus, when the first parameter needs to be determined, the control system 644 operates the first and second IR sources 604, 608 such that the first parameter can be measured (e.g., during a first time interval) and such that the second parameter can be measured (e.g., during a second time interval). As highlighted previously, the first and second parameters can be measured as and when needed. Thus, the 'indication' may cause the control system 644 to operate the first and second IR sources 604, 608 according to when IR radiation is needed to be produced so that the first and/or second parameters can be obtained. In an example, the 'indication' may be trigger such as an instruction from another device or system or a pre-determined instruction stored in the control system 644 to cause either the first or second IR sources 104, 108 to be provided with power in a particular time interval.

In some embodiments, the apparatus 600 further comprises a processing system 646 configured to derive the first and second parameters from the signal 618 and/or perform the comparison between the second parameter and the first parameter to obtain an indication of the concentration of the target gas in the gas sample region 614. The processing system 646 is depicted as being part of the apparatus 600 itself. In other embodiments, the functionality of the processing system 646 may be implemented by at least one external device (not shown) such as a user computer for analyzing the signal 618. In some embodiments, the functionality of the processing system 646 and the control system 644 may be implemented by the same device (e.g., at least one processor for executing instructions stored on a machine-readable medium for implementing the functionality of the processing system 464 and/or the control system 644).

There may be various ways to perform the 'comparison' between the first and second parameters to obtain an indication of a concentration (or partial pressure) of the target gas. In some embodiments, the indication of the concentration may be obtained by calculating a ratio between the second parameter and the first parameter (i.e., a 'ratiometric' calculation). In some embodiments, the indication of the calculation may be obtained based on a difference or some other comparison between the first and second parameters.

In some embodiments, the processing system 646 is configured to determine the first parameter from the signal 618 based on a range of signal values obtained during the first time interval. In some embodiments, the processing system 646 is configured to determine the second parameter from the signal based on a range of signal values obtained during the second time interval.

In some embodiments, the processing system 646 is configured to deconvolve a first signal component corresponding to the detected intensity due to the first IR beam 606 from a second signal component corresponding to the detected intensity due to the second IR beam 610 based on an indicated timing of the modulated intensity of the IR radiation produced by the first IR source 604 and the modulated intensity of the IR radiation produced by the second IR source 608. The 'indicated timing' may refer to the phase difference, frequency, etc. of the modulated first and second IR sources 604, 608. For example, if the phase difference, frequency, other synchronization information, etc. is known or can be determined by the processing system 646, the processing system 646 can then deconvolve the first and second signal components from each other. In an example, a measurement of the electrical resistance (such as may be obtained by the control system 644) across the first and second IR sources 604, 608 may be indicative of the timing of the modulated intensity of the IR radiation produced by each IR source 604, 608. It may be possible to determine which parts of the signal 618 corresponds to the first and second time intervals based on the indicated timing. In an example implementation, the processing system 646 may obtain the indicated timing from the control system 644. In another example implementation, the processing system 646 may send, to the control system 644, an indication of whether the first and/or second parameter is to be determined, as explained above. In either example, the control system 644 and the processing system 646 may be synchronized with each other to allow extraction of the first and second parameters within the appropriate time intervals.

After the convolution has been performed, the processing system 646 is configured to derive the first parameter from the first signal component and derive the second parameter from the second signal component.

In some embodiments, the deconvolution of the first signal component from the second signal component may be performed as explained below.

The processing system 646 may determine a contribution to the detected intensity due to the first IR beam 606 during the first and/or second time intervals. The processing system 646 may further determine a contribution to the detected intensity due to the second IR beam 610 during the first and/or second time intervals.

The contributions may be determined by accounting for any contribution to the detected intensity due to the first IR beam 606 during the second time interval and/or due to the second IR beam 610 during the first time interval based on a model of the level of IR radiation expected to be produced by the first and second IR sources 604, 608 over time according to the modulated power used to operate the first and second IR sources during the first and second time intervals. In other words, the 'model' may indicate how much IR radiation is expected to be produced over time by the first and second IR sources 604, 608, even when the supplied power is reduced or turned off. Thus, the model may allow the contribution to the detected intensity due to second IR beam 610 being present during the first time interval to be taken into account. The model may also allow the contribution to the detected intensity due to first IR beam 606 being present during the second time interval to be taken into account. The model may be based on knowledge or previous measurements of the IR radiation output by the first and second IR sources 606, 610. The model may depend on the type of source used. For example, an incandescent lamp may continue to produce IR radiation when hot even if it isn't powered whereas a laser diode may only produce IR radiation when powered, etc.

Once the contributions have been determined and their effect taken into account in each of the first and second time intervals, the first signal component may be extracted from the determined contribution to the detected intensity due to the first IR beam 606 (i.e., in the first time interval) and the second signal component may be extracted from the determined contribution to the detected intensity due to the second IR beam 610 (i.e., in the second time interval).

In some embodiments, the IR detection system 616 further comprises an IR detector 648 comprising an IR-sensitive detection area positioned to detect both the first and second IR beams 606, 610 using the same detection area. As depicted by FIG. 6, both the first and second IR beams 606, 610 are combined to follow the same beam path and are directed to the same detection area in the IR detection system 616. In this case, the same IR detector 648 is configured to detect the intensity of the first and second IR beams 606, 610 (to thereby produce the signal 618 corresponding to the combined intensity of the first and/or second IR beams 606, 610). In some cases, the IR detector 648 may comprise a single detection area or a plurality of detection areas aligned with the first and second IR beams 606, 610. In some cases, IR detection system 616 comprises a plurality of such IR detectors 648, all of which may be aligned with both the first and second IR beams 606, 610.

In contrast to an example approach of using one IR source and two or more channels of detection at one common mode of modulation, the depicted implementation of the apparatus 600 employs two IR sources 604, 608 and a common IR detection system 616. According to an example implementation of the apparatus 600, the two (or more) channels, C1 and C2, are time multiplexed for detection of the intensity of the IR radiation in each channel and de-multiplexed for the comparison (e.g., ratiometric calculation) between the level of attenuation of the IR radiation for the first channel (i.e., the 'reference channel') and the level of the attenuation of the IR radiation for the second channel (i.e., due to presence of the target gas constituent such as carbon dioxide).

In an example implementation of the apparatus 600, the IR detection system 616 comprises an IR detector 648 based on PbSe or InAsSb technology (which may be responsive to IR radiation in the wavelength range 2.5 to 10 µm). Any appropriate IR detection technology may be employed such as based on solid-state technology (e.g., in the case of PbSe or InAsSb technology) or another type of technology such as pyroelectric IR detection. Such IR detection technology may provide a fast response time suitable for certain applications like capnography. An example response time may be less than 10 ms, e.g., if the sampling rate is 100 Hz. Another example response time may be less than 1 ms. In an example implementation, the response time may be such that the IR detection system 616 is configured to obtain a plurality of measurements of the intensity of the first and/or second IR beam 606, 610 over a period of time corresponding to a phase of a respiratory cycle. In other words, the response time may be such that enough measurements (e.g., 50 measurements if the period of time is 5 seconds and a sampling rate of 100 Hz is employed) can be obtained over a relevant period of time.

Some IR detection technology may have strong temperature sensitivity, which could lead to uncalibrated or unreliable measurements of the detected intensity if the ambient temperature changes. However, the embodiments described herein may reduce or remove the need to perform calibration/compensation if the temperature changes because the measurements performed using the reference channel, C1, may take into account any variations such as temperature changes so that an accurate measurement of the channel, C2, can be obtained.

Figure 7:
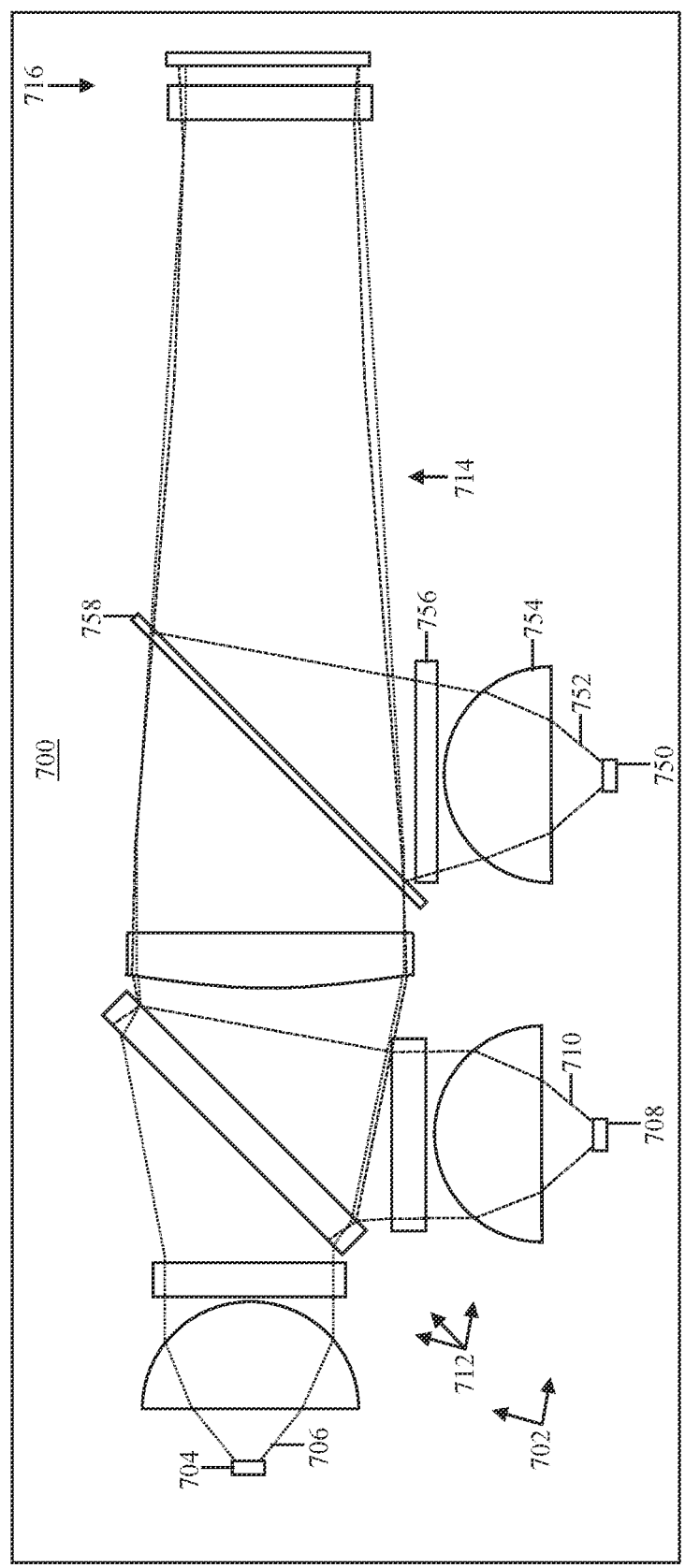
FIG. 7 is a schematic drawing of an apparatus for gas sensing according to an embodiment.

FIG. 7 is a schematic drawing of an apparatus 700 for gas sensing, in particular multi-gas sensing, according to an embodiment. The apparatus 700 may be used for the same or similar applications as described above although has additional functionality for multi-gas sensing. The apparatus 700 represents a possible variation of the apparatus 100 or 600. For example, features of the apparatus 700 may be provided in or combined with any embodiment or variation described in relation to the apparatus 100, 600, and vice versa. The apparatus 700 comprises the same features as the apparatus 100. In this regard, the features of the apparatus 700 have reference signs incremented by 600 compared with FIG. 1 or incremented by 100 compared with FIG. 6. Further features of the apparatus 700 are described below.

The IR generating system 702 further comprises a third IR source 750 configured to produce IR radiation for forming a third IR beam 752 in a third spectral band. The operation of the third IR source 750 is similar to the operation of the second IR source 708, as described below.

The third spectral band is associated with a third attenuation coefficient of a second target gas (e.g., for multi-gas sensing).

The third attenuation coefficient is higher than the first attenuation coefficient. Thus, the third attenuation coefficient may be higher, lower or the same as the second attenuation coefficient.

An intensity of the IR radiation produced by the third IR source 750 is modulatable in time in response to modulation of power for operating the third IR source 750.

The intensity of the IR radiation produced by the third source 750 is modulatable independently of the intensity of the IR radiation produced by the first and second IR sources 704, 708.

The beam manipulation system 712 is configured to combine a beam path of the first, second and third IR beams 706, 710, 752 and direct the first, second and third IR beams 706, 710, 752 along the beam path through the gas sample region 714.

In this embodiment, similar to the beam manipulation system 612 of FIG. 6, the beam manipulation system 712 further comprises a third collector lens 754 configured to collect the third IR beam 752. The third collector lens 754 may collimate or at least reduce the divergence of the third IR beam 752. The beam manipulation system 712 further comprises a third filter 756 (e.g., a long-pass, band-pass or short-pass filter) to spectrally filter the IR radiation produced by the third IR source 750 such that the third IR beam 752 has the 'third spectral content' after being filtered by the third filter 756.

With reference to the beam manipulation system 612 of FIG. 6, the beam manipulation system 712 further comprises an additional beam combiner 758 (similarly arranged to the beam combiner 638 of FIG. 6) configured to transmit the first beam 706 (and the second IR beam 710) and reflect the third IR beam 752 (or reflect the first and second IR beams 706, 710 and transmit the third IR beam 752, etc.) such that the first, second and third IR beams 706, 710, 752 are combined to have the same beam path (or substantially the same beam path). Due to the arrangement of the first, second and third IR sources 704, 708, 750 with respect to the beam manipulation system 712, the first, second and third IR beams 706, 710, 752 are directed along the same (or similar) beam path through the gas sample region 714.

The IR detection system 716 is configured to detect an intensity of the first, second and third IR beams 706, 710, 752 after passage through the gas sample region 714. The signal produced by the IR detection system 716 may be further indicative of the detected intensity due to the third IR beam 752. A third parameter derived from a third time interval (which may or may not overlap with the first and/or second time intervals) of the signal may be indicative of a level of attenuation of the third IR beam 752 in the gas sample region 714. A comparison (e.g., a ratiometric calculation, difference, etc.) between the third parameter and the first parameter may be indicative of a concentration of the second target gas in the gas sample region 714.

The apparatus 700 may be used for multi-gas sensing. For example, the (first) target gas may be a certain gas constituent (such as carbon dioxide) and the second target gas may be another gas constituent (such as an anesthetic gas) in a gas sample. Such apparatus 700 may provide accurate measurements of the concentration of different gas constituents over a relatively broad operating temperature range in a compact/robust package that may have a relatively low power consumption.

Figure 8:
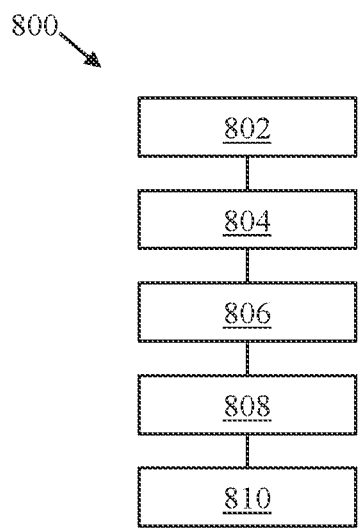
FIG. 8 refers to a method of gas sensing according to an embodiment.

FIG. 8 refers to a method 800 of gas sensing according to an embodiment. In this embodiment, the method 800 implements the functionality of the apparatus 100. In other embodiments, corresponding methods may implement the functionality of other apparatus described herein such as apparatus 600 and related embodiments. Reference is made to the apparatus 100 in the description of the method 800.

The method 800 comprises, at block 802, producing, using a first IR source 104, IR radiation for forming a first IR beam 106 in a first spectral band.

The method 800 comprises, at block 804, producing, using a second IR source 108, a second IR beam 110 in a second spectral band.

The first spectral band is associated with a first attenuation coefficient of a target gas.

The second spectral band is associated with a second attenuation coefficient of the target gas.

The second attenuation coefficient is higher than the first attenuation coefficient.

An intensity of the IR radiation produced by the first IR source 104 is modulatable in time in response to modulation of power for operating the first IR source 104.

An intensity of the IR radiation produced by the second IR source 108 is modulatable in time in response to modulation of power for operating the second IR source 108.

The intensity of the IR radiation produced by the first IR source 104 is modulatable independently of the intensity of the IR radiation produced by the second IR source 108.

The method 800 further comprises, at block 806, combining, using a beam manipulation system 112, a beam path of the first and second IR beams 106, 110 to direct the first and second IR beams 106, 110 along the beam path through a gas sample region 114.

The method 800 further comprises, at block 808, detecting, using an IR detection system 116, an intensity of the first and second IR beams 106, 110 after passage through the gas sample region 114.

The method 800 further comprises, at block 810, producing, using the IR detection system 116, a signal 118. The signal 118 is indicative of the detected intensity due to the first IR beam 106. A first parameter derived from a first time interval of the signal 118 is indicative of a level of attenuation of the first IR beam 106 in the gas sample region 114. The signal 118 is further indicative of the detected intensity due to the second IR beam 110. A second parameter derived from a second time interval of the signal 118 is indicative of a level of attenuation of the second IR beam 110 in the gas sample region 114.

A comparison between the second parameter and the first parameter is indicative of a concentration of the target gas in the gas sample region 114.

According to certain embodiments described herein, the apparatus 100, 600, 700, related embodiments and associated methods may multiplex at least two independently modulated IR beams 606, 610 by combining the IR beams

606, 610 to facilitate measurement of attenuation of the IR beams 606, 610 by a target gas with reduced or minimal temperature dependence. Certain embodiments may allow a signal 118, 618 from an IR detection system 616 for detecting the intensity of at least two IR beams 606, 610 to be de-multiplexed based on a synchronization with the IR radiation output profile of each IR source 604, 608 (e.g., based on a model of the IR source 604, 608 resistance and/or knowledge of the type of IR source 604, 608). Certain embodiments may enable the fast and/or accurate signal 618 de-multiplexing from the IR detection system 616. Certain embodiments may provide apparatus 100, 600 that can operate at relatively low power (e.g., due to reduced number of components and/or independent modulation of the IR sources 604, 608) in a compact and/or robust package while also providing accurate measurements over a relatively broad ambient temperature range. Certain embodiments such as apparatus 700 may be deployed for multi-gas sensing applications. Certain embodiments refer to apparatus 100, 600, 700 and a method 700 that may be deployable in a range of scenarios such as clinical and/or emergency scenarios while still providing rapid and accurate measurements (e.g., for capnography applications).

Figure 9:
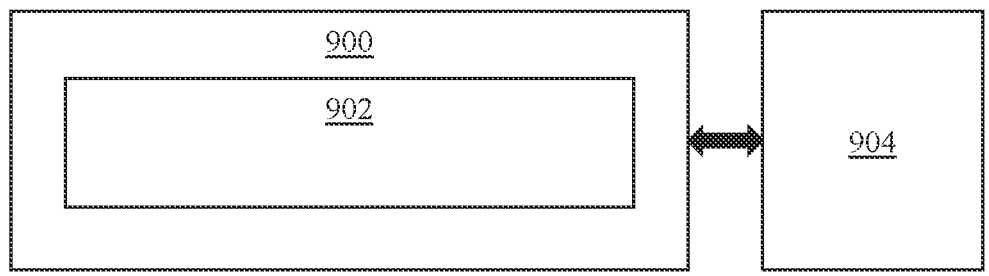
FIG. 9 is a schematic drawing of a machine-readable medium for facilitating gas sensing according to an embodiment.

FIG. 9 shows a non-transitory machine-readable medium 900 for facilitating gas sensing according to an embodiment. The non-transitory machine-readable medium 900 comprises instructions 902 which, when executed on at least one processor 904, cause the at least one processor 904 to implement certain methods associated with the operation of the apparatus 100, 600, 700 and/or the implementation of the method 700. In some embodiments, the non-transitory machine-readable medium 900 may be implemented by the control system 644 and/or processing system 646 (e.g., to facilitate synchronization of the systems 644, 646 or otherwise facilitate the operation of any of the embodiments described herein).

Figure 10:
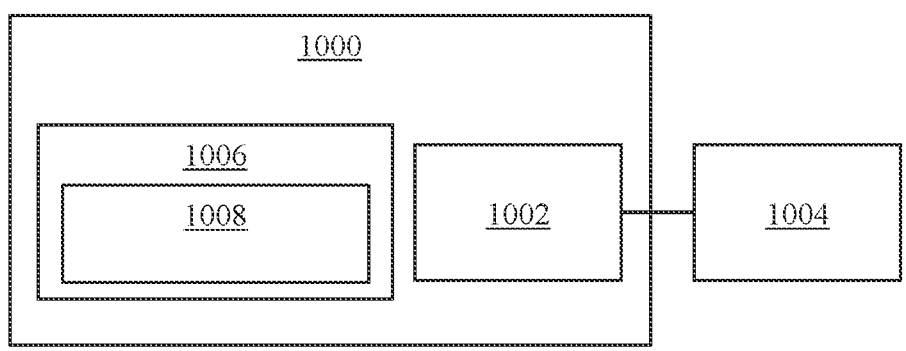
FIG. 10 is a schematic drawing of apparatus for facilitating gas sensing according to an embodiment.

FIG. 10 shows apparatus 1000 for facilitating gas sensing according to an embodiment. The apparatus 1000 comprises at least one processor 1002 (e.g., implemented by a computing device such as the control system 644 and/or processing system 646). The at least one processor 1002 is communicatively coupled to an interface 1004 for communicating data (e.g., exchanging synchronization information such as the 'indicated timing', receiving the raw data signal 118, 618 and/or sending an indication of the concentration of the target gas).

The apparatus 1000 further comprises a non-transitory machine-readable medium 1006 storing instructions 1008 readable and executable by the at least one processor 1002 to perform a method corresponding to certain methods such as implemented by the control system 644 and/or processing system 646 (e.g., to facilitate synchronization of the systems 644, 646 or otherwise facilitate the operation of any of the embodiments described herein).

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices, and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine-readable instructions may, for example, be executed by a general-purpose computer, a special purpose computer, an embedded processor, or processors of other programmable data processing devices to realize the functions described in the description and diagrams. In particular, a processor or processing circuitry, or a module thereof, may execute the machine-readable instructions. Thus, functional modules of apparatus and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine-readable instructions may also be stored in a computer readable storage that can guide the computer or other programmable data processing devices to operate in a specific mode.

Such machine-readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or

The invention claimed is:

1. An apparatus, comprising:
    an infrared (IR) generating system comprising:
        a first IR source configured to produce IR radiation for forming a first IR beam in a first spectral band; and
        a second IR source configured to produce IR radiation for forming a second IR beam in a second spectral band, wherein:
        an intensity of the IR radiation produced by the first IR source is modulatable in time in response to modulation of power for operating the first IR source;
        an intensity of the IR radiation produced by the second IR source is modulatable in time in response to modulation of power for operating the second IR source; and
        the intensity of the IR radiation produced by the first IR source is modulatable independently of the intensity of the IR radiation produced by the second IR source;
    a beam manipulation system configured to combine a beam path of the first and second IR beams and direct the first and second IR beams along the beam path through a gas sample region; and
    an IR detection system configured to detect an intensity of the first and second IR beams after passage through the gas sample region, and wherein the IR detection system is configured to produce a signal indicative of:
        the detected intensity due to the first IR beam, wherein a first parameter derived from a first time interval of the signal is indicative of a level of attenuation of the first IR beam in the gas sample region; and
        the detected intensity due to the second IR beam, wherein a second parameter derived from a second time interval of the signal is indicative of a level of attenuation of the second IR beam in the gas sample region,
    wherein the signal comprises a convolution of a first signal component corresponding to the detected intensity due to the first IR beam and a second signal component corresponding to the detected intensity due to the second IR beam, wherein:
        the first parameter is derivable from the signal based on a deconvolution of first and second signal components in the first time interval; and
        the second parameter is derivable from the signal based on a deconvolution of first and second signal components in the second time interval, and
    wherein a concentration of a target gas in the gas sample region is indicated by a comparison between the second parameter and the first parameter.

2. The apparatus of claim 1, wherein:
    the target gas is at least one constituent of gas for inhalation inhaled by a subject and/or at least one constituent of gas exhaled by the subject; and
    the apparatus is configured to obtain an indication of the concentration of the at least one constituent in a gas sample obtained from the gas inhaled by the subject and/or the gas exhaled by the subject.

3. The apparatus of claim 1, wherein the intensity of the IR radiation produced by the first and second IR sources is modulatable such that at least one of:
    (i) the intensity of the IR radiation produced by the first IR source is modulated at the same frequency as, but out of phase with, the intensity of the IR radiation produced by the second IR source;
    (ii) the intensity of the IR radiation produced by the first IR source is modulated at a different frequency to the intensity of the IR radiation produced by the second IR source;
    (iii) the intensity of the IR radiation produced by the first IR source has a higher intensity than the IR radiation produced by the second IR source during the first time interval;
    (iv) the intensity of the IR radiation produced by the second IR source has a higher intensity than the IR radiation produced by the first IR source during the second time interval;
    (v) the IR radiation produced by the second IR source is produced continuously or repeatedly over a period of time, wherein the signal produced by the IR detection system over the period of time is indicative of a plurality of values for the second parameter, wherein the plurality of values for the second parameter are indicative of the level of attenuation of the second IR beam in the gas sample region over the period of time, and wherein the plurality of values for the second parameter are indicative of any variation of the concentration of the target gas over the period of time; or
    (vi) the IR radiation produced by the first IR source is produced at least once before, during and/or after the period of time, wherein the signal produced by the IR detection system at least once before, during and/or after the period of time is indicative of at least one value for the first parameter, wherein the at least one value for the first parameter is indicative of the level of attenuation of the first IR beam in the gas sample region.

4. The apparatus of claim 3, wherein the period of time corresponds to a phase of a respiratory cycle.

5. The apparatus of claim 1, wherein the beam manipulation system is configured to combine the beam path of the first and second IR beams through the gas sample region such that an optical axis of the first and second IR beams is collinear in the gas sample region.

6. The apparatus of claim 1, further comprising:
    a control system configured to modulate the power for operating the first and second IR sources to independently modulate the intensity of the IR radiation produced by the first IR source and the intensity of the IR radiation produced by the second IR source.

7. The apparatus of claim 6, wherein the control system is configured to, in response to receiving an indication of whether the first parameter and/or the second parameter is to be determined, modulate the intensity of the IR radiation produced by the first IR source and the intensity of the IR radiation produced by the second IR source such that the IR detection system produces the signal indicative of the first parameter and/or the second parameter.

8. The apparatus of claim 1, further comprising:
    a processing system configured to derive the first and second parameters from the signal and/or perform the comparison between the second parameter and the first parameter to obtain the indication of the concentration of the target gas in the gas sample region.

9. The apparatus of claim 8, wherein the processing system is configured to:
    determine the first parameter from the signal based on a range of signal values obtained during the first time interval; and/or
    determine the second parameter from the signal based on a range of signal values obtained during the second time interval.

10. The apparatus of claim 8, wherein the processing system is configured to:
   deconvolve the first signal component corresponding to the detected intensity due to the first IR beam from the second signal component corresponding to the detected intensity due to the second IR beam based on an indicated timing of the modulated intensity of the IR radiation produced by the first IR source and the modulated intensity of the IR radiation produced by the second IR source; and
   derive the first parameter from the first signal component and derive the second parameter from the second signal component.

11. The apparatus of claim 1, wherein the IR detection system comprises an IR detector comprising an IR-sensitive detection area positioned to detect both the first and second IR beams using the same detection area.

12. The apparatus of claim 1, wherein:
   the IR generating system further comprises a third IR source configured to produce IR radiation for forming a third IR beam in a third spectral band;
   an intensity of the IR radiation produced by the third IR source is modulatable in time in response to modulation of power for operating the third IR source;
   the intensity of the IR radiation produced by the third IR source is modulatable independently of the intensity of the IR radiation produced by the first and second IR sources;
   the beam manipulation system is configured to combine a beam path of the first, second and third IR beams and direct the first, second and third IR beams along the beam path through the gas sample region; and
   the IR detection system is configured to detect an intensity of the first, second and third IR beams after passage through the gas sample region, and wherein the signal produced by the IR detection system is further indicative of:
   the detected intensity due to the third IR beam, wherein a third parameter derived from a third time interval of the signal is indicative of a level of attenuation of the third IR beam in the gas sample region, and wherein the concentration of a second target gas in the gas sample region is further indicated a comparison between the third parameter and the first parameter.

13. A respiratory monitoring system, comprising:
   a respiratory gas sampling system configured to obtain a respiratory gas sample; and
   the apparatus of claim 1, wherein the respiratory gas sampling system is configured to provide the obtained respiratory gas sample in the gas sample region of the apparatus, wherein the indication of the concentration of the target gas is produced in the obtained respiratory gas sample.

14. A method, comprising:
   producing, using a first infrared (IR) source, IR radiation for forming a first IR beam in a first spectral band;
   producing, using a second IR source, a second IR beam in a second spectral band, wherein:
      the first spectral band is associated with a first attenuation coefficient of a target gas;
      the second spectral band is associated with a second attenuation coefficient of the target gas;
      the second attenuation coefficient is higher than the first attenuation coefficient;
      an intensity of the IR radiation produced by the first IR source is modulatable in time in response to modulation of power for operating the first IR source;
      an intensity of the IR radiation produced by the second IR source is modulatable in time in response to modulation of power for operating the second IR source; and
      the intensity of the IR radiation produced by the first IR source is modulatable independently of the intensity of the IR radiation produced by the second IR source;
   combining, using a beam manipulation system, a beam path of the first and second IR beams to direct the first and second IR beams along the beam path through a gas sample region;
   detecting, using an IR detection system, an intensity of the first and second IR beams after passage through the gas sample region; and
   producing, using the IR detection system, a signal indicative of:
      the detected intensity due to the first IR beam, wherein a first parameter derived from a first time interval of the signal is indicative of a level of attenuation of the first IR beam in the gas sample region; and
      the detected intensity due to the second IR beam, wherein a second parameter derived from a second time interval of the signal is indicative of a level of attenuation of the second IR beam in the gas sample region,
   wherein the signal comprises a convolution of a first signal component corresponding to the detected intensity due to the first IR beam and a second signal component corresponding to the detected intensity due to the second IR beam, wherein:
      the first parameter is derivable from the signal based on a deconvolution of first and second signal components in the first time interval; and
      the second parameter is derivable from the signal based on a deconvolution of first and second signal components in the second time interval; and
   determining a concentration of the target gas in the gas sample region by comparing the second parameter and the first parameter.

15. An apparatus, comprising:
   an infrared (IR) generating system comprising a first IR source configured to produce IR radiation for forming a first IR beam in a first spectral band, and a second IR source configured to produce IR radiation for forming a second IR beam in a second spectral band;
   a beam manipulation system configured to combine a beam path of the first and second IR beams and direct the first and second IR beams along the beam path through a gas sample region;
   a control system configured to modulate power for operating the first IR source to modulate an intensity of the IR radiation produced by the first IR source in time, and to independently modulate an intensity of the IR radiation produced by the second IR source in time;
   an IR detection system configured to detect an intensity of the first and second IR beams after passage through the gas sample region, wherein the IR detection system is configured to produce a signal indicative of the detected intensity due to the first IR beam and the detected intensity due to the second IR beam, wherein the signal comprises a convolution of a first signal component corresponding to the detected intensity due to the first IR beam and a second signal component corresponding to the detected intensity due to the second IR beam; and
   a processing system configured to:

derive a first parameter from the signal based on a deconvolution of the first and second signal components in a first time interval of the signal indicative of a level of attenuation of the first IR beam in the gas sample region;

derive a second parameter from the signal based on a deconvolution of the first and second signal components in a second time interval of the signal indicative of a level of attenuation of the second IR beam in the gas sample region; and perform a comparison between the second parameter and the first parameter, wherein the comparison is indicative of a concentration of target gas in the gas sample region.

16. The apparatus of claim 15, wherein:
the target gas is at least one constituent of gas for inhalation by a subject and/or at least one constituent of gas exhaled by the subject.

17. The apparatus of claim 15, wherein the control system is configured to modulate the power for operating the first IR source and the second IR source such that at least one of:
(i) the intensity of the IR radiation produced by the first IR source is modulated at the same frequency as, and out of phase with, the intensity of the IR radiation produced by the second IR source;
(ii) the intensity of the IR radiation produced by the first IR source is modulated at a different frequency than the intensity of the IR radiation produced by the second IR source;
(iii) the intensity of the IR radiation produced by the first IR source has a higher intensity than the IR radiation produced by the second IR source during the first time interval; or
(iv) the intensity of the IR radiation produced by the second IR source has a higher intensity than the IR radiation produced by the first IR source during the second time interval.

18. The apparatus of claim 15, wherein the beam manipulation system is further configured to combine the beam path of the first and second IR beams through the gas sample region such that an optical axis of the first and second IR beams is collinear in the gas sample region.

19. The apparatus of claim 15, wherein the processing system is further configured to:
determine the first parameter from the signal based on a range of signal values obtained during the first time interval; and/or
determine the second parameter from the signal based on a range of signal values obtained during the second time interval.

20. The apparatus of claim 15, wherein the IR detection system comprises an IR detector comprising an IR-sensitive detection area positioned to detect the first IR beam and the second IR beam using the same detection area.

* * * * *